US011911582B2

(12) United States Patent
Cheng et al.

(10) Patent No.: US 11,911,582 B2
(45) Date of Patent: Feb. 27, 2024

(54) DEVICES AND METHODS FOR WOUND-CONFORMAL GUIDANCE OF BIOPRINTER PRINTHEAD

(71) Applicants: SUNNYBROOK RESEARCH INSTITUTE, Toronto (CA); THE GOVERNING COUNCIL OF THE UNIVERSITY OF TORONTO, Toronto (CA)

(72) Inventors: Richard Cheng, Toronto (CA); Gertraud Eylert, Vienna (AT); Sijin He, Beijing (CN); Jean-Michel Gariépy, Toronto (CA); Navid Hakimi, Toronto (CA); Marc G. Jeschke, Toronto (CA); Axel Guenther, Toronto (CA)

(73) Assignees: SUNNYBROOK RESEARCH INSTITUTE, Toronto (CA); THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 1222 days.

(21) Appl. No.: 16/517,388

(22) Filed: Jul. 19, 2019

(65) Prior Publication Data
US 2020/0023172 A1 Jan. 23, 2020

Related U.S. Application Data

(60) Provisional application No. 62/700,715, filed on Jul. 19, 2018.

(51) Int. Cl.
B29C 67/00 (2017.01)
A61F 2/10 (2006.01)
(Continued)

(52) U.S. Cl.
CPC .......... *A61M 35/003* (2013.01); *A61F 2/105* (2013.01); *A61L 27/20* (2013.01); *A61L 27/225* (2013.01);
(Continued)

(58) Field of Classification Search
CPC . A61M 35/003; A61M 2210/04; A61L 27/26; A61L 27/54; A61L 2300/412; A61L 2430/34; A61F 2240/002; B29C 64/393
See application file for complete search history.

(56) References Cited

U.S. PATENT DOCUMENTS 11,168,295 B2 * 11/2021 Hakimi ................. C12M 21/08
2020/0040291 A1 * 2/2020 Hakimi ................. C12M 21/08

OTHER PUBLICATIONS

Williams, Felicia et.al. (2009). The leading causes of death after burn injury in a single pediatric burn center. Critical Care. 13. R183. Doi:10.1186/cc8170. 7 pages.
(Continued)

*Primary Examiner* — Ryan M Ochylski
(74) *Attorney, Agent, or Firm* — HILL & SCHUMACHER

(57) ABSTRACT

Disclosed herein is an instrument that enables the in situ formation of architected planar biomaterials and tissues by translating a printer head along a deposition surface such as a patient having burn injuries. In handheld embodiments of the instrument, cell-laden biopolymer solutions are perfused through a moving microfabricated printer head and deposited onto a stationary planar surface or a wound. The printer head may be translated via a drive mechanism. A soft deformable roller mitigates further damage to the injured area of skin as it rolls over it and a gimbal mechanism to which the printer head is attached is in contact with the injured tissue but is configured so that the printer head while in contact with tissue, does not exert undue pressure on the would area.

36 Claims, 13 Drawing Sheets

(51) Int. Cl.
- A61L 27/20 (2006.01)
- A61L 27/22 (2006.01)
- A61L 27/24 (2006.01)
- A61L 27/26 (2006.01)
- A61L 27/54 (2006.01)
- A61M 35/00 (2006.01)
- B29C 64/209 (2017.01)
- B29C 64/25 (2017.01)
- B29C 64/264 (2017.01)
- B29C 64/393 (2017.01)
- B33Y 30/00 (2015.01)
- B33Y 50/02 (2015.01)
- C12M 1/32 (2006.01)
- B29L 31/00 (2006.01)

(52) U.S. Cl.
CPC .............. *A61L 27/24* (2013.01); *A61L 27/26* (2013.01); *A61L 27/54* (2013.01); *B29C 64/209* (2017.08); *B29C 64/25* (2017.08); *B29C 64/264* (2017.08); *B29C 64/393* (2017.08); *B33Y 30/00* (2014.12); *B33Y 50/02* (2014.12); *C12M 33/06* (2013.01); *A61F 2240/002* (2013.01); *A61L 2300/412* (2013.01); *A61L 2300/414* (2013.01); *A61L 2430/34* (2013.01); *A61L 2430/40* (2013.01); *A61M 2210/04* (2013.01); *B29K 2995/0056* (2013.01); *B29L 2031/753* (2013.01)

(56) References Cited

OTHER PUBLICATIONS

Gibran, Nicole (2013). "The ABA's Pursuit of Excellence: A Long and Winding Road . . . to Your Door". Burn Care & Research. vol. 34. pp. 361-363.

Hakimi, Navid et al. Handheld Skin Printer: In-Situ Formation of Planar Biomaterials and Tissues & Electronic Supplementary Material. Lab on a Chip, 2018, 18, 1440-1451 10.1039/C7LC01236E.

\* cited by examiner

DEVICES AND METHODS FOR WOUND-CONFORMAL GUIDANCE OF BIOPRINTER PRINTHEAD

FIELD

The invention relates to a printhead attached to a bioprinting unit to homogeneously deposit temperature sensitive biomaterial sheets over large physiologically relevant topographies in situ without damage to the wound substrate.

BACKGROUND

Nearly 500,000 burn injuries require medical treatment each year, with approximately 40,000 hospitalizations and 3,400 deaths annually (Gibran N S, 2013). Severe thermal injury over a large area of the skin, roughly 20% total body surface area (TBSA) or greater, results in acute systemic responses collectively known as burn shock, which contribute to 67%±30% of death after the burn injury (Williams F N, 2009). Within short time, requiring temporary coverage with allografts, or tissues taken from a living or deceased human donor, and prepare the wound bed for autograft, is difficult for these patients.

Alternatively, many skin substitutes have been developed based on both natural and synthetic polymers. Experimental product SkinGun™ from RenovaCare (Gerlach, 2011) has provided a method to spray a water-based solution containing autogenous stem cell onto the wound, and showed positive result clinically. However, this technology is lacking deterministic control over the spatial organization of cells and biopolymers. Additionally, the lack of supporting extracellular matrix components (ECM) co-delivered in a 3D context indicates the reliance of delivered and host cells to generate and remodel the microenvironment. Previous work (Hakimi, 2018) involving the handheld skin printer has enabled the on-site formation of wound-adhesive skin substitutes using microfluidics cartridge to spatially organized cell-laden biopolymer solutions. Biomaterial choices reported there were limited to ionic crosslinking (alginate) or enzymatic (thrombin) which were amenable to cell growth conditions but associated with poor construct structure and high degradation. The use of biomaterials that utilized temperature induced gelation mechanisms would extend the available biomaterials for bioprinting.

Although the previously published in vivo data demonstrated that the handheld skin printer enables the direct distribution of wound-adhesive biomaterials onto a wound bed, it was limited to well-defined small rectangular defects due to the positioning of the wheel flanking the microfluidic extrusion cartridge. To cover a large area like the shape of a realistic TBSA burn, the printhead would require repetitive side by side deposition without overlap or interruption. With the previous iteration of the driven roller located on side of the microfluidics device, the handheld skin printer cannot provide coverage over large, irregularly shaped wounds.

Printing over a larger wound area in a physiological context is associated with printing over territory that contains arbitrary curvatures. For instance, human finger is shaped like a parabolic cylinder with 9 mm radius of curvature with sharp angular changes. Human forearms and thighs are elliptic paraboloid (an upside-down oval cup with vertex), while the lower back is hyperbolic paraboloid (shape of Pringles/a saddle). The previous iteration of the handheld skin printer was equipped with a rigid printhead, achieving consistent sheet deposition only on planar surfaces.

The skin wound of which the bioprinter is in contact with is also fragile, indicating a need to minimize the pressure exerted on the wound bed during the printing process. Since homogeneity of the deposited material is reliant on the speed of deposition, a mechanism is also required to maintain traction between the soft wheel and the deposition surface during the lateral motion of the bioprinter during the deposition process.

Therefore, a need exists in the field for a bioprinter printhead to homogeneously deposit temperature sensitive biomaterial sheets over large physiologically relevant topographies in situ without damage to the wound substrate.

SUMMARY

Disclosed herein is an instrument that enables the in situ formation of architected planar biomaterials and tissues by translating a printer head along a deposition surface. In handheld embodiments of the instrument, cell-laden biopolymer solutions are perfused through a moving microfabricated printer head and deposited onto a stationary planar surface or a wound. The printer head may be translated via a drive mechanism. Different embodiments of the instrument are disclosed for in vivo application in small animals, as well as for large animal and clinical application. A stationary embodiment of the instrument is well suited for the continuous formation and roll-to-roll processing of planar biomaterials and tissues.

The present disclosure provides a bioprinter for controlled in-situ formation and deposition of any one or combination of biopolymeric sheets, therapeutic agents and planar tissues on surfaces on surfaces, comprising:

a) support frame and a gimbal attached to the support frame and a printhead attached to the gimbal, the printhead including a first array of extrusion channels and a gelation means located with respect to said first array such that in operation the gimbal positions the printhead such that the first array is in physical contact with the surface regardless of the contour of the surface, an end section of the printhead having a width W such that the first and second arrays span the width W;

b) a first reservoir containing a biopolymer, the first reservoir being operably attached to said frame, the first array of extrusion channels being in flow communication with the first reservoir such that the biopolymer is configured to be extruded onto the surface, a first dispensing mechanism associated with the first reservoir being configured to dispense biopolymer at a flow rate of QM;

c) a drive mechanism attached to the frame including a soft roller, the drive mechanism such that when activated by the operator, the printhead is driven along the surface at a preselected velocity V by said soft roller; and d) a controller connected to said drive mechanism and the first dispensing mechanism and the gelation means and programmed such upon activating the drive mechanism, and when the first dispenser includes biopolymer, said dispensing mechanism dispenses biopolymer at the flow rate QM a layer of thickness t and said gelation means gelates said biopolymer on said surface.

The drive mechanism may be configured to provide variable velocities V, and wherein the controller is programmed with instructions to control the at first dispensing mechanism to responsively adjust the flow rate QM such that for a given velocity V the flow rate conditions are maintained. If more than one dispenser are included with accompanying dispensing mechanism, the controller may be programmed with instructions to control all the dispensing mechanisms.

The exit section of the printhead may include an overhanging section extending outwardly from a top surface of the second array with overhanging protruding section extending outwardly from the exit section by a length L.

The first array of extrusion channels may be in flow communication with the first reservoir via a bifurcating channel network comprised of a first channel connected to the first reservoir which bifurcates into two channels which further bifurcates until a final number of channels equals a number of extrusion channels in the first array, and an end of each channel is adjacent an end of a corresponding extrusion channel in the first array.

The hydraulic diameters of the channels in the bifurcating channel networks decrease from each inlet to each exit going from the reservoir to said printer head in accordance with Murray's law. Murray's law determines the width and depth of microfluidic channel transfer networks such that the energy cost of transport and maintenance is minimized, similar to vascular networks in animals.

The bioprinter may further comprise a handle for allowing a user to grasp and use the bioprinter during dispensing operations so that the bioprinter is a handheld bioprinter.

The printhead interface may be attached to the gimbal and the printhead may be removably attachable to the printhead interface.

The printhead may be secured to the printhead interface by a printhead quick release mechanism.

The soft roller may be removably attachable to the drive mechanism.

The soft roller may be secured to the drive mechanism by a roller quick release mechanism.

The first reservoir may be removably attachable to the frame.

When in operation the gimbal may be configured such that the printhead exerts a force on the surface that is independent of the force that the soft roller exerts on the surface.

The gimbal may be a two-axis gimbal to provide two (2) degrees of freedom motion.

The gelation means may be a liquid gelation means including a second reservoir containing a gelation liquid, the second reservoir being attached to the frame, the printhead having a second array of extrusion channels being in flow communication with the second reservoir such that the gelation liquid is configured to be extruded along with the extruded biopolymer, and a second dispensing mechanism associated with the second reservoir being configured to dispense the liquid at a flow rate of QC, wherein the controller is connected to the second dispensing mechanism and programmed such upon activating the drive mechanism, the second dispensing mechanism dispenses biopolymer at the flow rate QM.

The second array of extrusion channels may be in flow communication with the second reservoir via a bifurcating channel network comprised of a first channel connected to the second reservoir which bifurcates into two channels which further bifurcates until a final number of channels equals a number of extrusion channels in the second array, and an end of each channel is adjacent an end of a corresponding extrusion channel in the second array.

The second reservoir may be removably attachable to the frame.

The gelation means may be a light induced gelation means including a light source configured to emit light and a light emitter in optical communication with said light source, wherein said biopolymer is photopolymerizable, and wherein the controller may be connected to the light source and programed such upon activating the drive mechanism, the light source emits light and the light emitter directs the light onto the surface such that the biopolymer gelates via photo cross-linking.

The light source may be a plurality of light sources and said light emitter is a plurality of light emitters.

The light source may be a remote light source attached to the frame and the light gelation means further includes a light transmission means configured to transmit light from said light source to said light emitter.

The bioprinter light transmission means may comprise at least one optical fiber.

The light source and the light emitter may be a combined light source and emitter operably attached to the printhead.

The bioprinter may further include a temperature control system configured to control the temperature of said biopolymer.

The temperature control system may include a printhead temperature control means is operably attached to said printhead, and said printhead temperature control means connected to said controller and programed such that the user can control the temperature of said biopolymer in said printhead.

The temperature control system may include a first temperature control jacket operably attached to said frame, said first temperature control jacket is connected to said controller and programed to adjust the temperature of said first temperature control jacket such that the user can control the temperature of said biopolymer in said first reservoir.

The temperature control system one of a solid-state thermoelectric device, a temperature regulation loop containing a working heat exchange fluid, or phase-change materials.

The gelation means may be a temperature induced gelation means, and wherein the biopolymer is cooled in the printhead such that the biopolymer gelates upon being dispensed onto said surface.

The gimbal may be a three-axis gimbal to provide three (3) degrees of freedom motion.

The bioprinter may further comprise a preselected additional number of reservoirs, each reservoir having a dispensing mechanism associated therewith.

Each reservoir may be heated or cooled by a single heating or cooling source.

Each reservoir may be heated or cooled independently of the other reservoirs by separate heaters or coolers.

The therapeutic agents may be precursors of biopolymeric sheets and planar tissues, cells, proteins, drugs etc.

The at least first reservoir may be a syringe.

The bioprinter may be configured, shaped and sized to be held by a human hand, or it may be configured, shaped and sized to be held by a robotic hand or end effector.

The present disclosure also provides method of applying therapeutic agents to injured skin using the device according to claim 1, comprising:
  selecting a liquid mixture having a therapeutic agent mixed therein and filing said at least first reservoir,
  programming the controller to provide a preselected flow rate of the therapeutic agent being dispensed from the reservoir and a preselected velocity of the drive mechanism of the soft roller; and
  activating both said first dispensing mechanism to dispense the therapeutic agent and said drive mechanism to rotate said soft roller causing said bioprinter to dispense said therapeutic agent.

There can be several dispensers for dispensing multiple therapeutic agents or other liquids, reagents, solvents, cells, proteins to mention a few.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
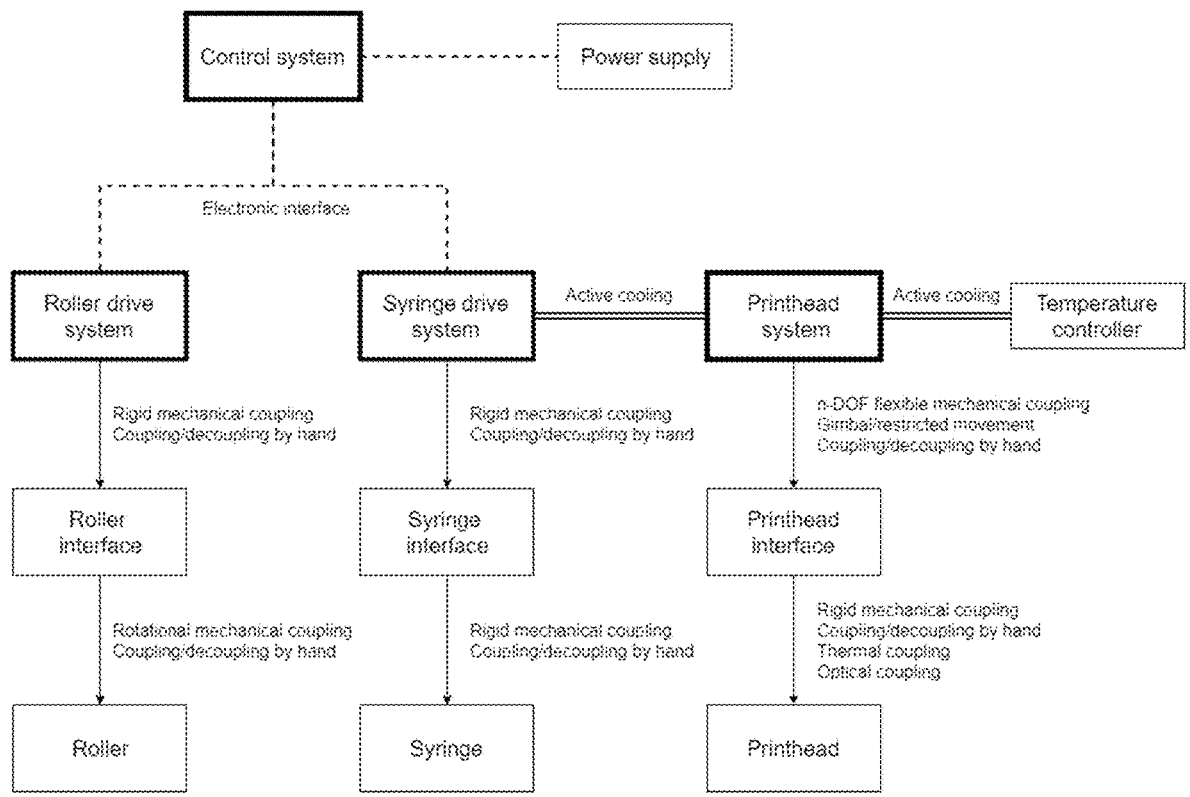
FIG. 1 is a block diagram showing four primary module components: the control system, the roller drive system, the syringe drive system, and the printhead system. The power supply provides power to the control system, where it controls the roller drive system and the syringe drive system through an electronic interface. The syringe system and printhead system are linked to a temperature control loop to provide active temperature regulation. The roller drive system is comprised of the roller interface and the roller; the syringe drive system is comprised of the syringe interface and the syringe; and the printhead system is comprised of the printhead interface and the printhead.
Figure 2:
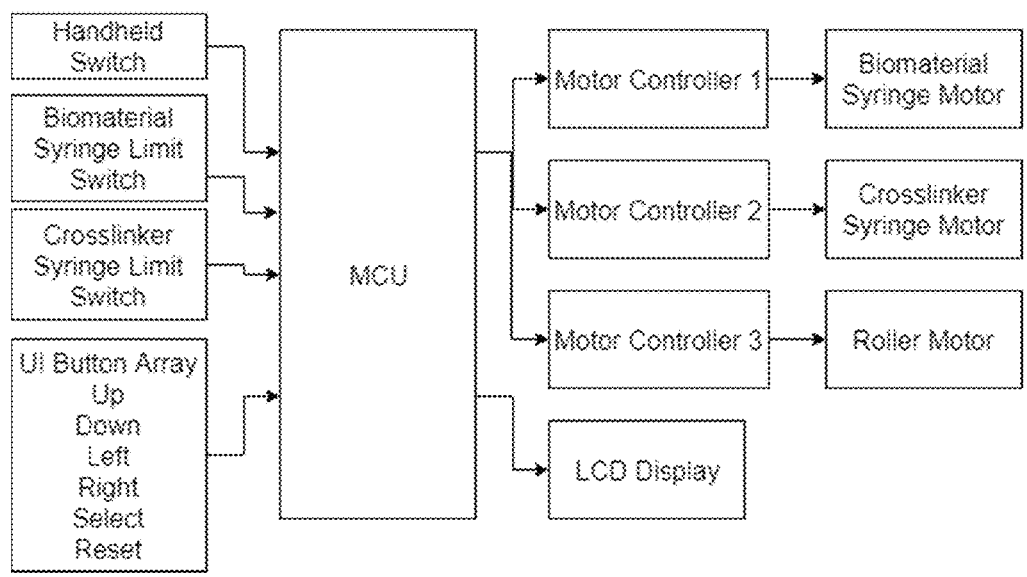
FIG. 2 is a block diagram showing inputs towards the main control unit and resulting outputs. Inputs include the handheld switch, the biomaterial limit switch, the crosslinker limit switch, and the user interface button array. Outputs include the motor controller driving the biomaterial syringe drive system, the motor control driving the crosslinker syringe drive system, the motor controller driving the roller system, and the LCD display to show operating conditions including flow rates and roller translation speed.
Figure 3:
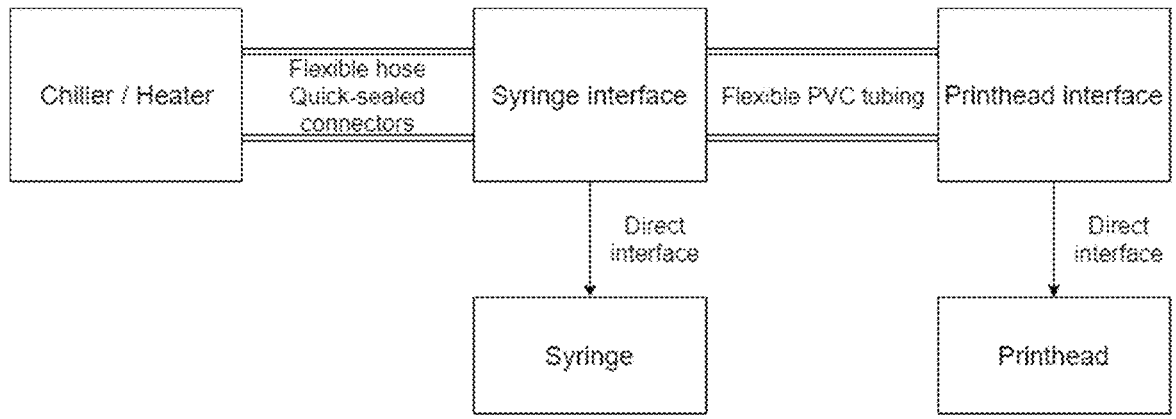
FIG. 3 is a block diagram showing the temperature loop from the chiller/heater to the syringe interface and the printhead interface. The chiller/heater is connected to the syringe interface via a flexible hose and quick-sealed connectors. The syringe interface is connected to the printhead interface via a flexible PVC tubing. The syringe is directly interfacing the syringe interface; similarly, the printhead is directly in contact with the printhead interface.
Figure 4:
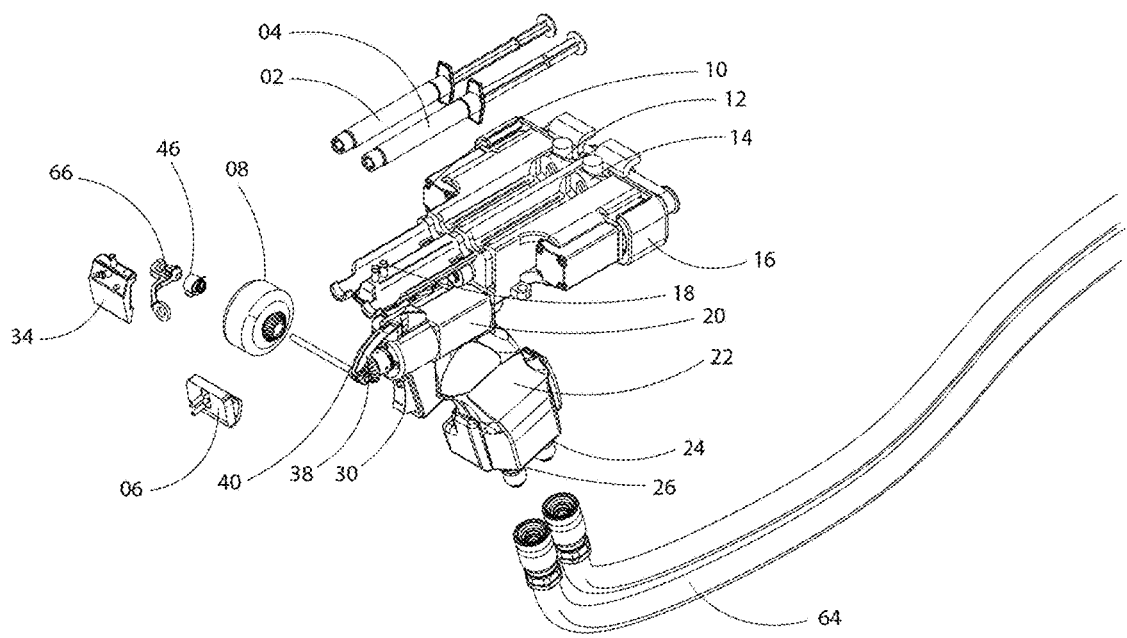
FIG. 4 is a line drawing, exploded isotropic view, of the handheld bioprinter embodiment.
Figure 5:
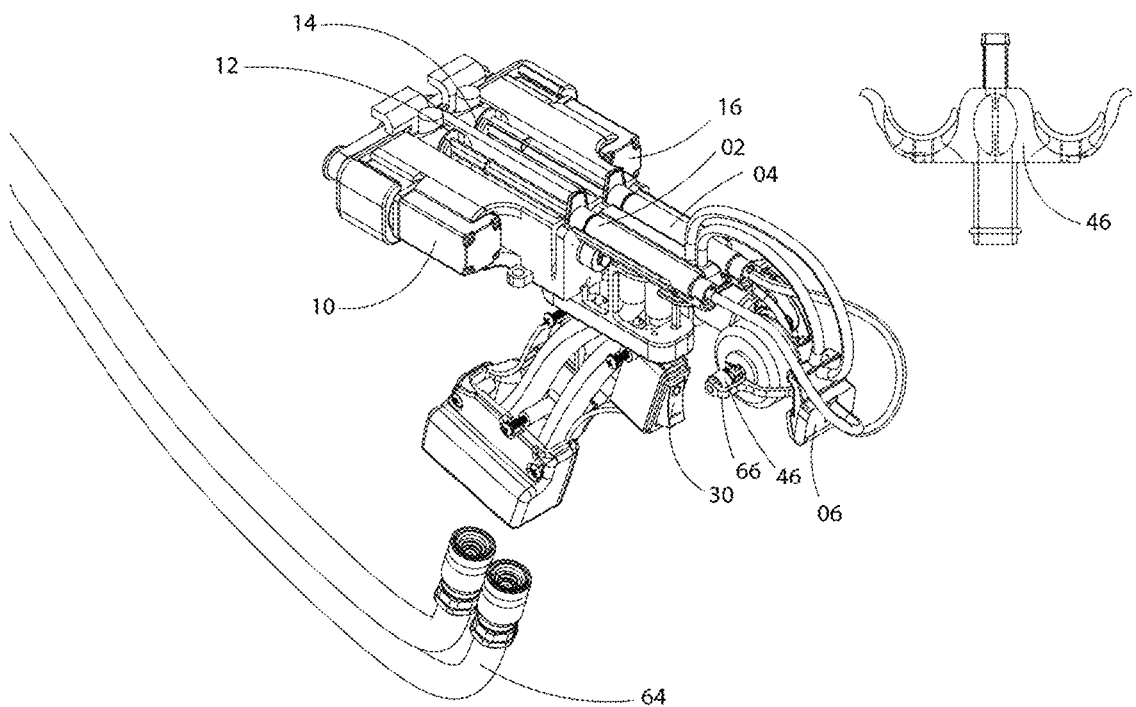
FIG. 5 is a line drawing, assembled isotropic view, of the handheld bioprinter embodiment with connection to the chiller detached, and a front view of the syringe interface.
Figure 6:
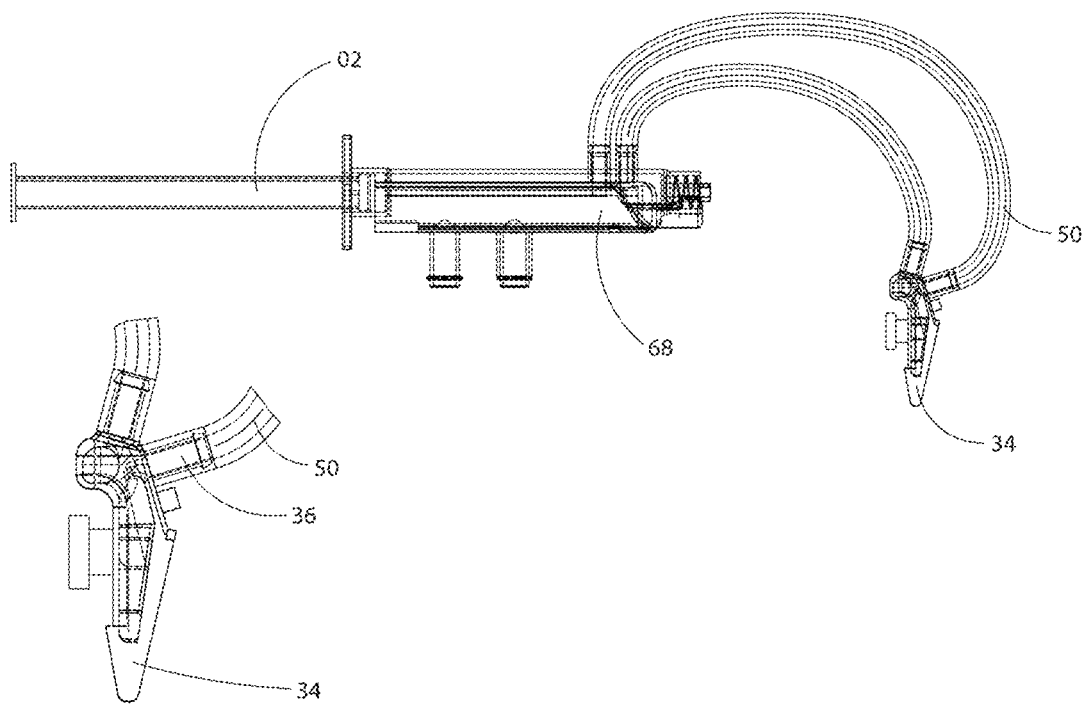
FIG. 6 is a line drawing, side view of the two temperature-controlled components: the syringe interface and the printhead interface. Connections between the two temperature-controlled components are made via coolant tubing.
Figure 7:
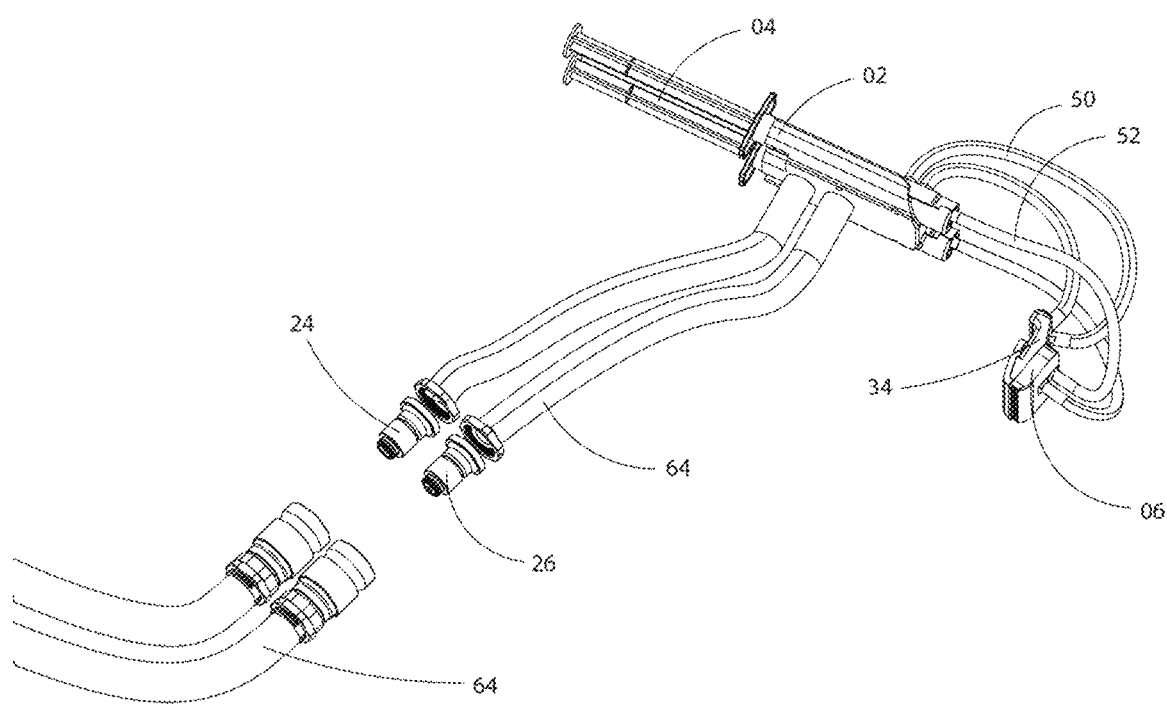
FIG. 7 is a line drawing, isotropic view, of internal temperature loop system inside the handheld bioprinter. The syringe interface is in contact with the syringe, and the printhead interface is in contact with the printhead. The coolant enters the handheld printer through one coolant port, travels through the scaffold, tubing, and bracket, then exits through the other coolant port, where it then re-enters the external chiller.
Figure 8:
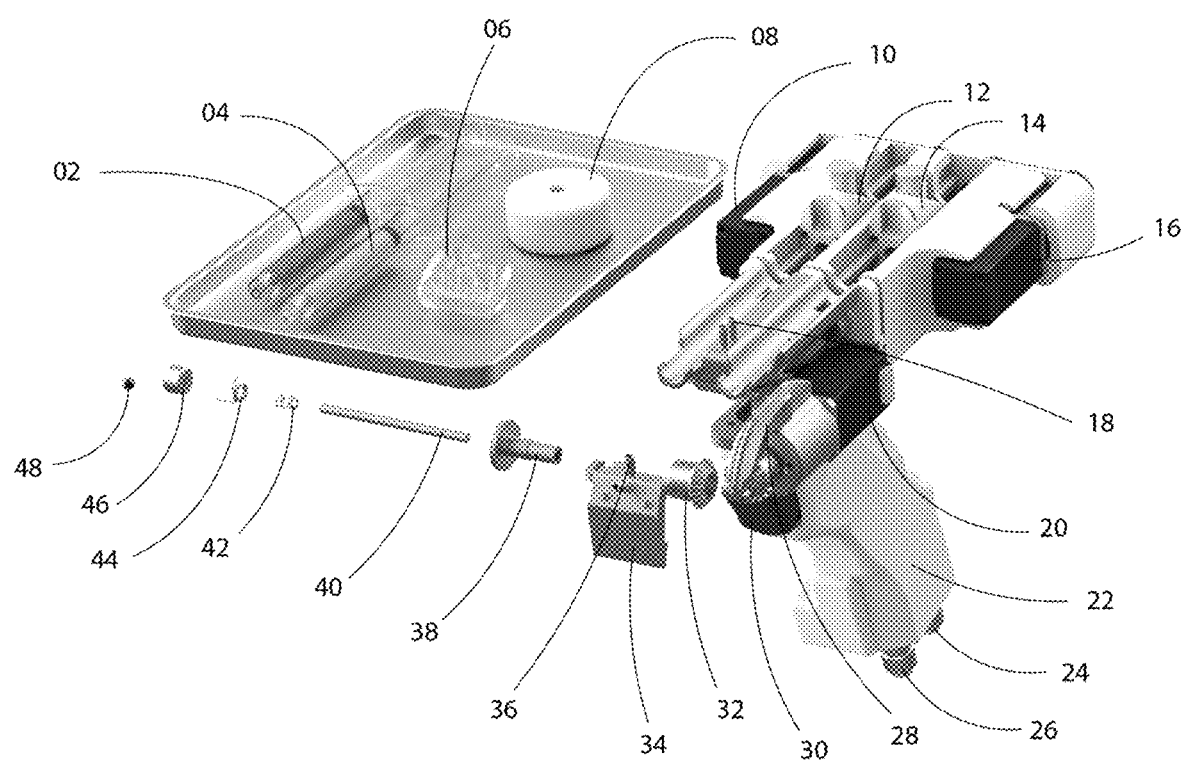
FIG. 8 is a schematic illustration, isotropic view, of the handheld bioprinter embodiment with printhead components disassembled. The handheld printer is comprised of two categories of components. The single-use disposables are located on the tray, and include the cell AND biomaterial containing syringes (02), crosslinker containing syringes (04), microfluidic printhead (06), and the roller (08). The remainder are repeated-use and sterilizable components.
Figure 9:
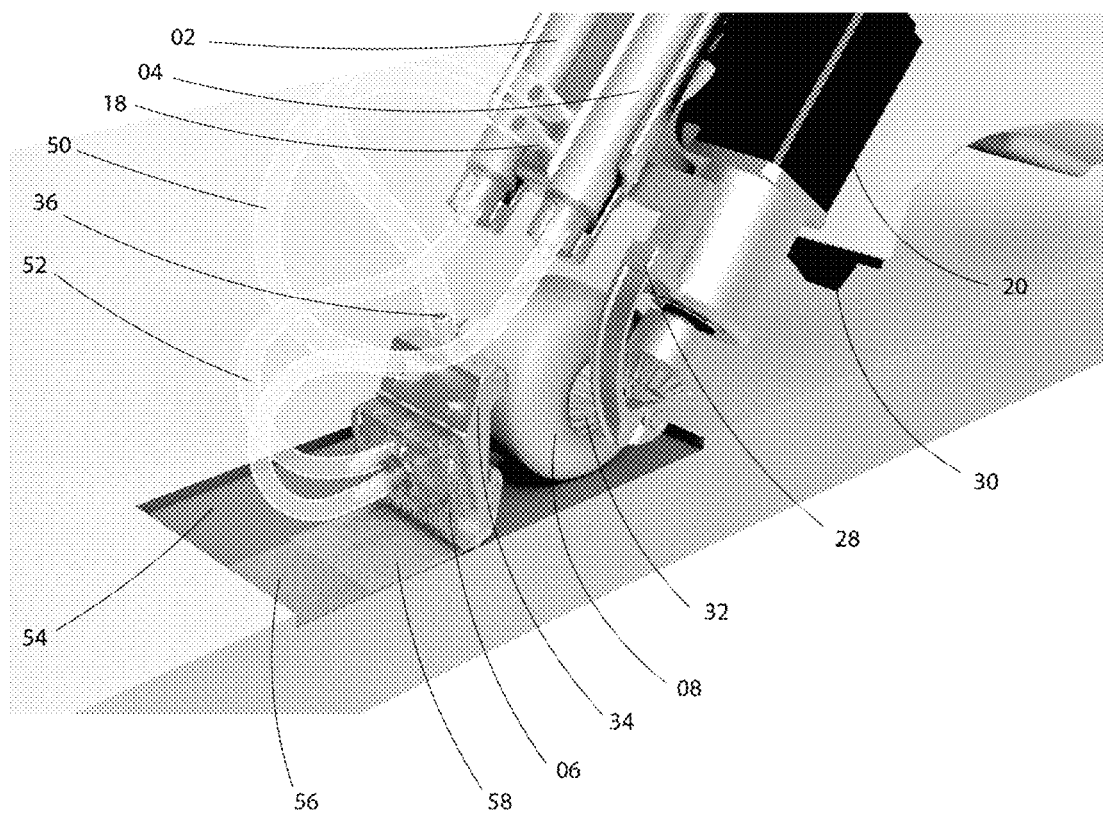
FIG. 9 is a schematic illustration, isotropic view, of handheld bioprinter embodiment with drive mechanism behind printer head. The extrusion process is initiated when the button on the handheld interface is triggered (30). The syringe containing cells and biomaterials exit the syringe (02), pass through the material tubing (52), and into the microfluidic printhead (06), where it forms a sheet (56). Simultaneously, the crosslinker containing syringe (04), pass through another set of material tubing (52), and into the microfluidic printhead (06), where it forms an additional sheet (58) directly on top of the biomaterial sheet. The crosslinker gels the material directly on the wound (54). Additionally, the coolant flows from the scaffold coolant port (18), through the coolant tubing (50), through the printhead coolant port (36), and into the printhead interface (34). At the same time, the roller (08), which is driven by the wheel stepper motor (20) and coupled to the bevel gear (32) and frame (28), activates and translates across the wound.
Figure 10:
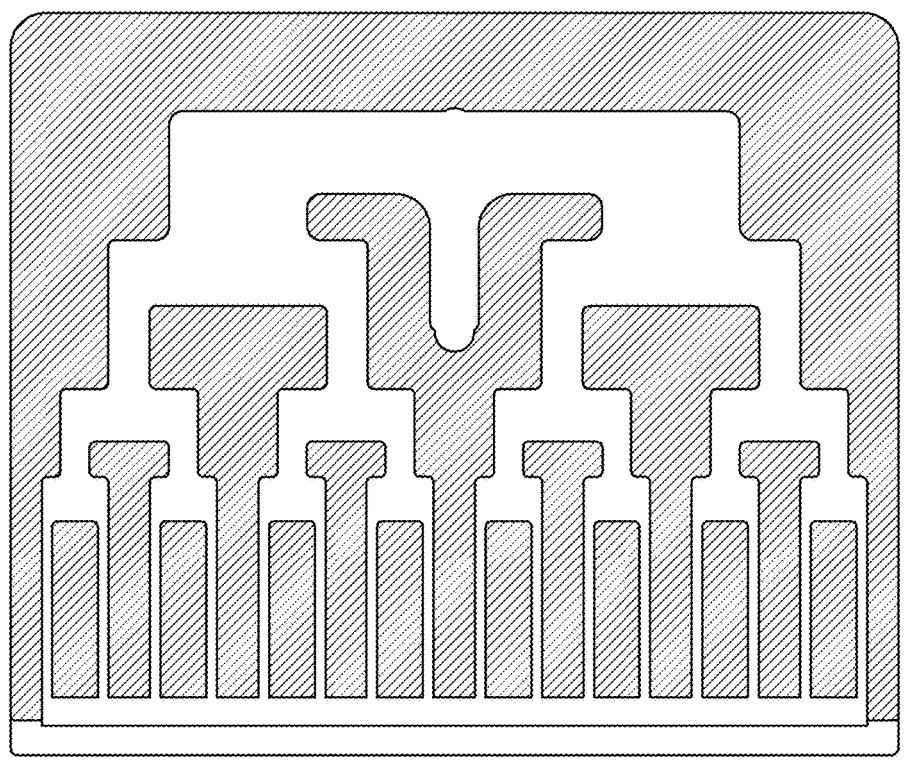
FIG. 10 is a schematic illustration, front view, of the internal structure of the microfluidic device which is attached to the holder. The internal structure of the printhead in this embodiment contains a branching architecture, where a single channel splits into 2, 4, 8, and 16 daughter channels before exiting as a sheet.
Figure 11:
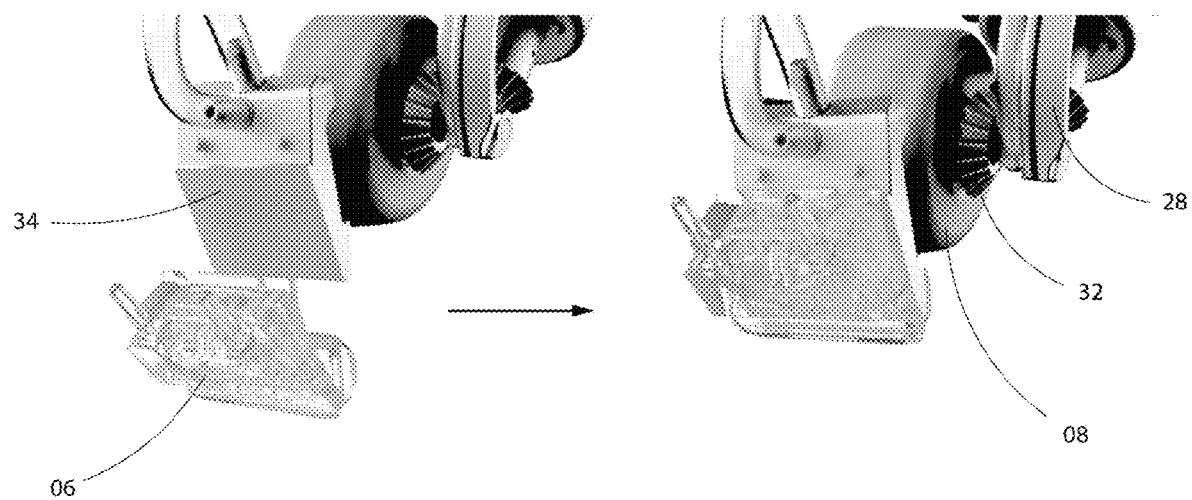
FIG. 11 is a schematic illustration, isotropic view, of the process of the printhead attaching onto the printhead interface. The printhead can be clipped onto the printhead interface without additional tools in this embodiment to allow rapid assembly and disassembly.
Figure 12:
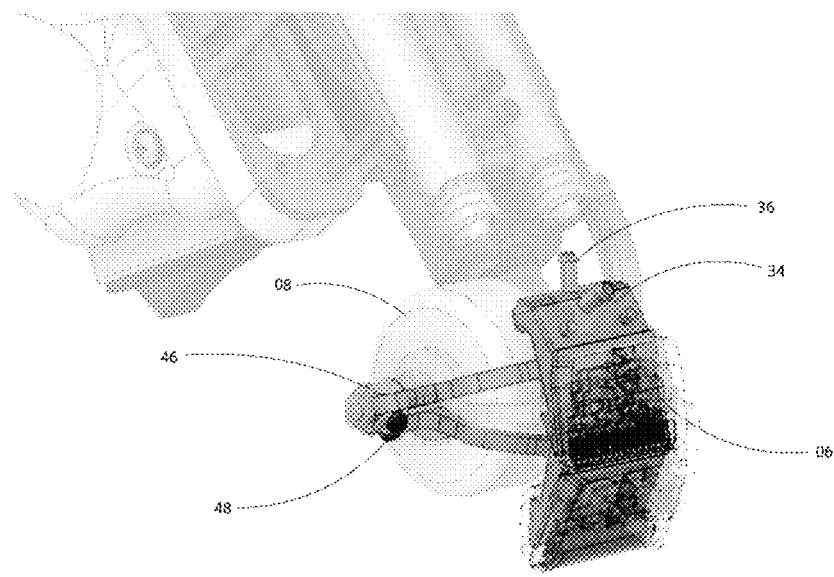
FIG. 12 is a schematic illustration, isotropic view, of the printhead attached to the printhead interface with a mechanical mechanism to enable rotational freedom in the Z-axis of rotation. The printhead (06) is attached to the printhead interface (34) in front of the roller (08) and contains a mechanical component enabling rotational freedom about the Z-axis of rotation about the rod and spring coupler (46). The starting position of the printhead is determined by the position of the set screw (48).
Figure 13:
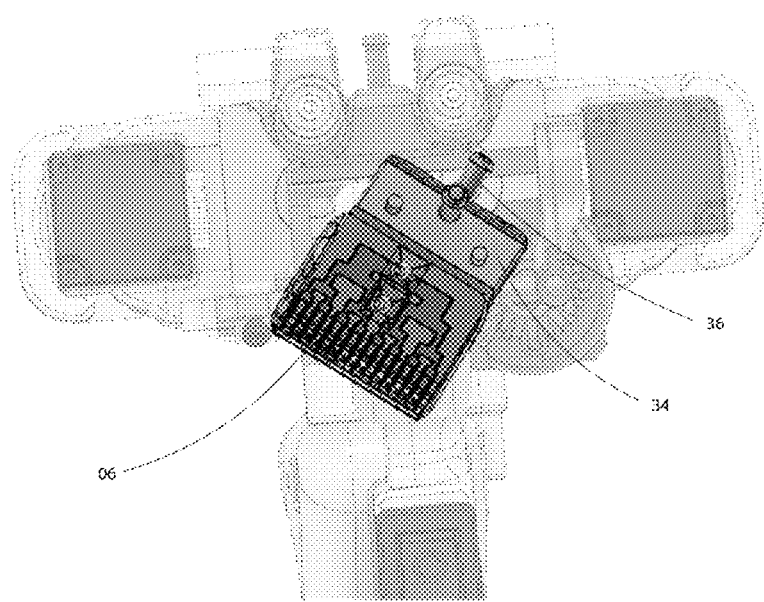
FIG. 13 is a schematic illustration, isotropic view, of the printhead attached to the printhead interface with a mechanical mechanism to enable rotational freedom in the X-Y axis of rotation. The printhead (06) is attached to the printhead interface (34) and contains a mechanical component enabling rotational freedom about the X-Y axis of rotation.
Figure 14:
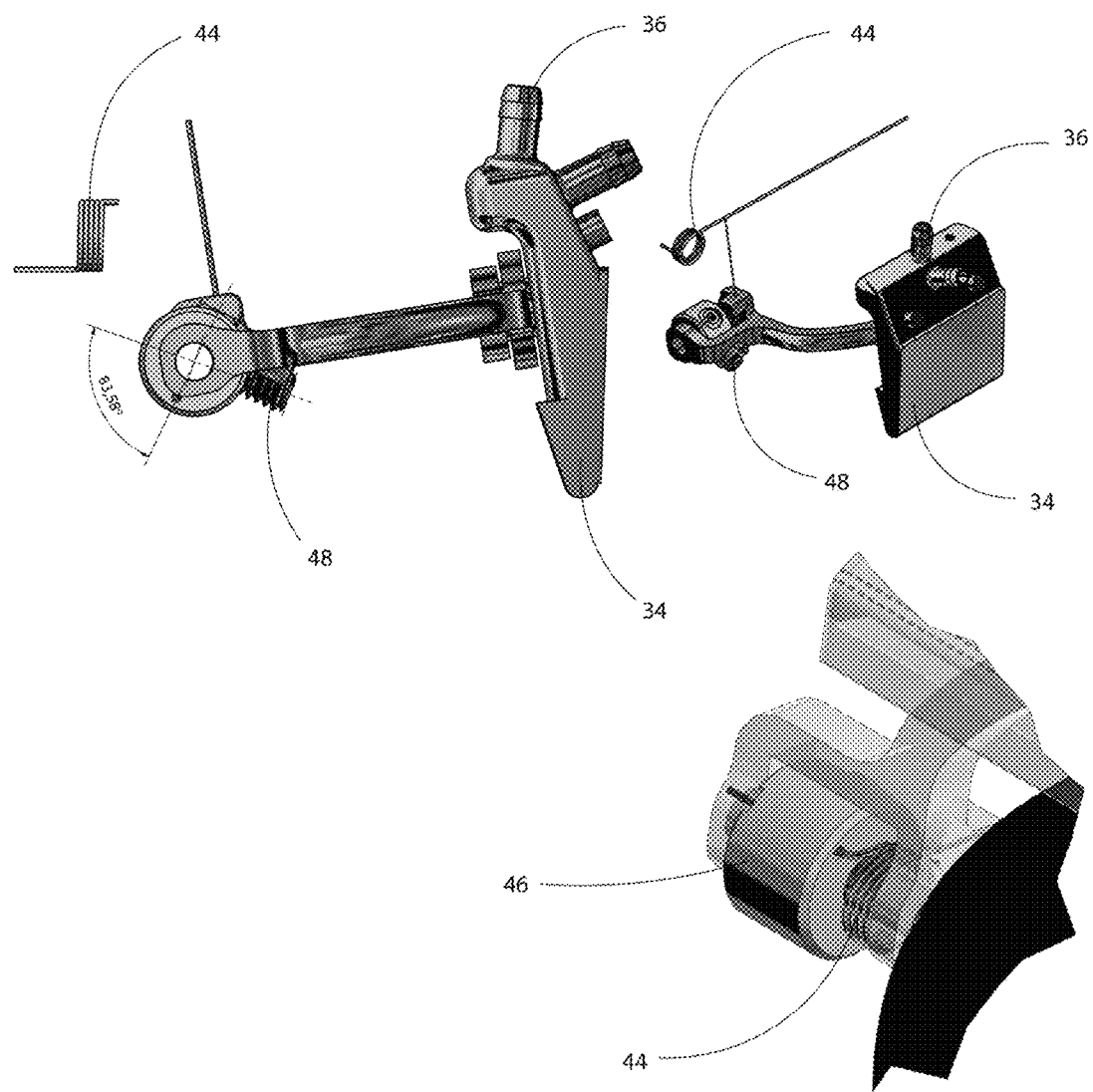
FIG. 14 is a schematic illustration, side view, of the holder design, where a torsional spring allows rotational freedom in the X-Y and Z axis of rotation to accommodate topographical heterogeneities. The printhead interface (34) starting position is determined by the set screw position (48). Rotational freedom is permitted by the torsional spring (44) held by the spring coupler (46). The two-axis gimbal design in this embodiment guides the printhead over arbitrarily large and inclined wounds.
Figure 15:
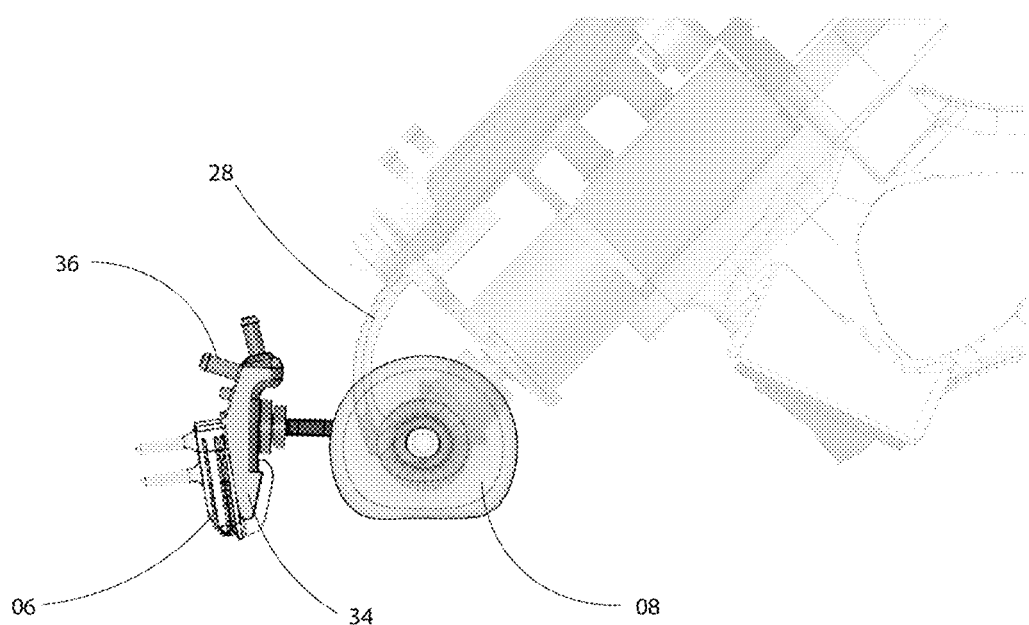
FIG. 15 is a schematic illustration, side view, of the roller on a separate axis than the printhead and the printhead interface. The roller, which is a soft silicone wheel in this embodiment (08), is held in position by the wheel frame (28) situated on a separate axis than the printhead interface (34) and the attached printhead (06). The soft wheel achieves a large contact area with the wound to reduce the contact pressure and increase the traction.
Figure 16:
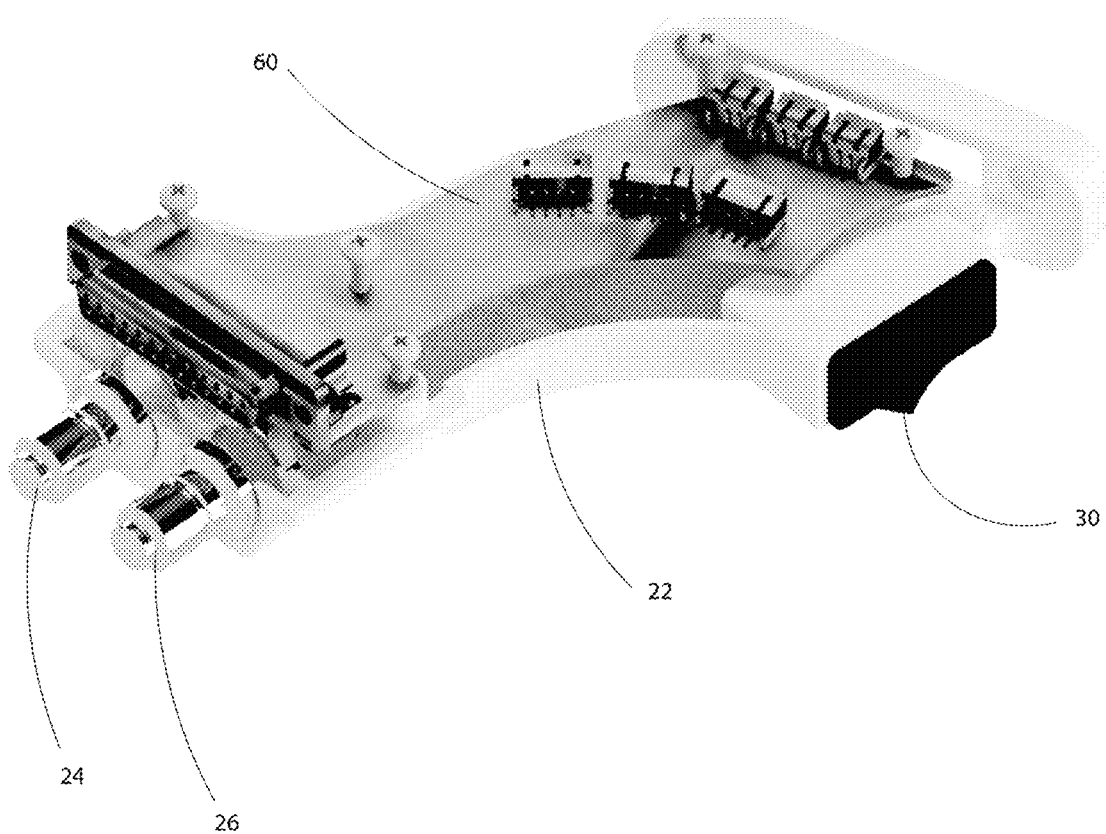
FIG. 16 is a schematic illustration, isotropic view, of the open handle with the toggle switch controlling on-board syringe systems. The coolant lines are compactly situated behind the printed circuit board. The handheld interface, which is a handle in this embodiment (22), contains an on-board printed circuit board (60) which is toggled by the switch (30). Coolant lines flow in and out of the handheld printer via the two coolant ports (24, 26).
Figure 17:
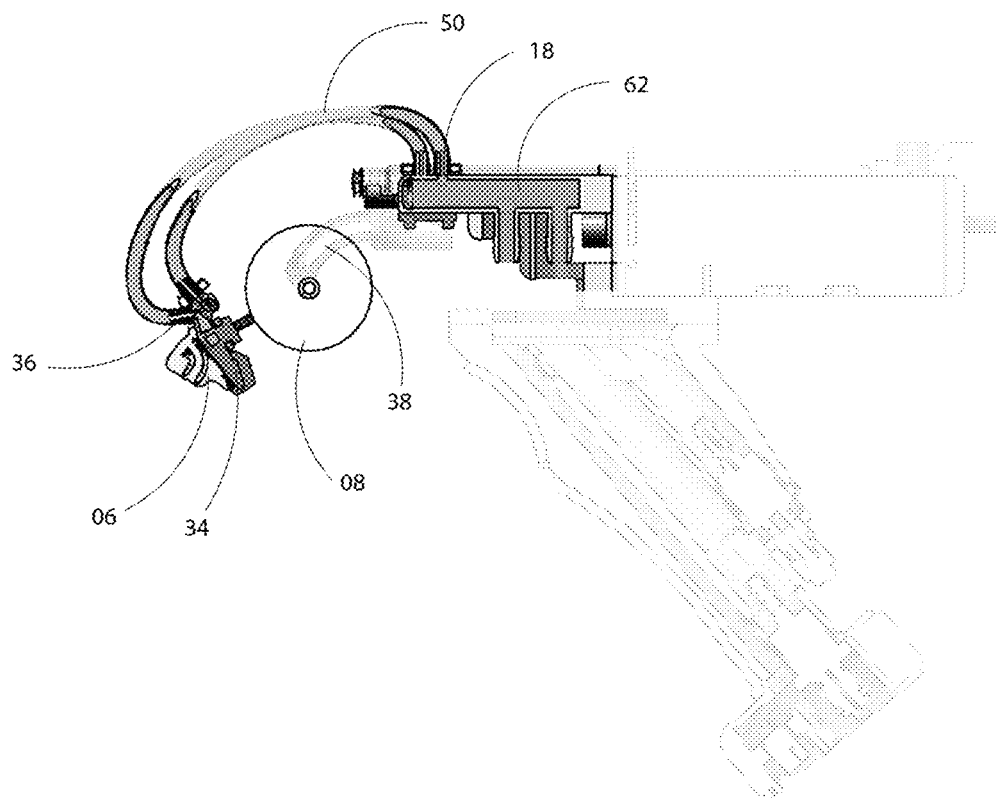
FIG. 17 is a schematic illustration, side view, of the handheld printer with coolant entering the device and filling the cavity in the scaffold, traveling through the coolant tubing, then filling the hollow holder and exiting the handheld printer. The handheld printer is temperature controlled in this embodiment to allow in situ deposition of biopolymer solutions and bioinks with temperature induced gelation (eg. Collagen, elastin, and other extracellular matrix materials). The coolant (62) enters the handheld printer scaffold, then travels through the scaffold port (18), through coolant tubing (50), into the printhead interface coolant port (36), and into the printhead interface (34) where it controls the temperature of the printhead (06).
Figure 18:
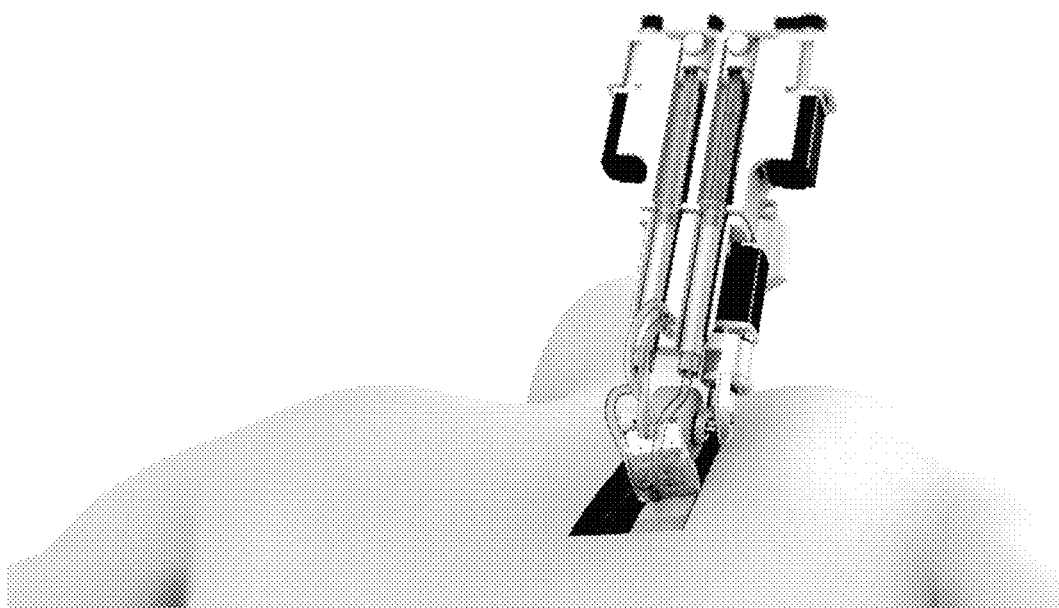
FIG. 18 is a schematic illustration, in-context view of the handheld printer. The handheld printer is designed for direct delivery of cell and biomaterial containing materials onto a patient wound surface.
Figure 19:
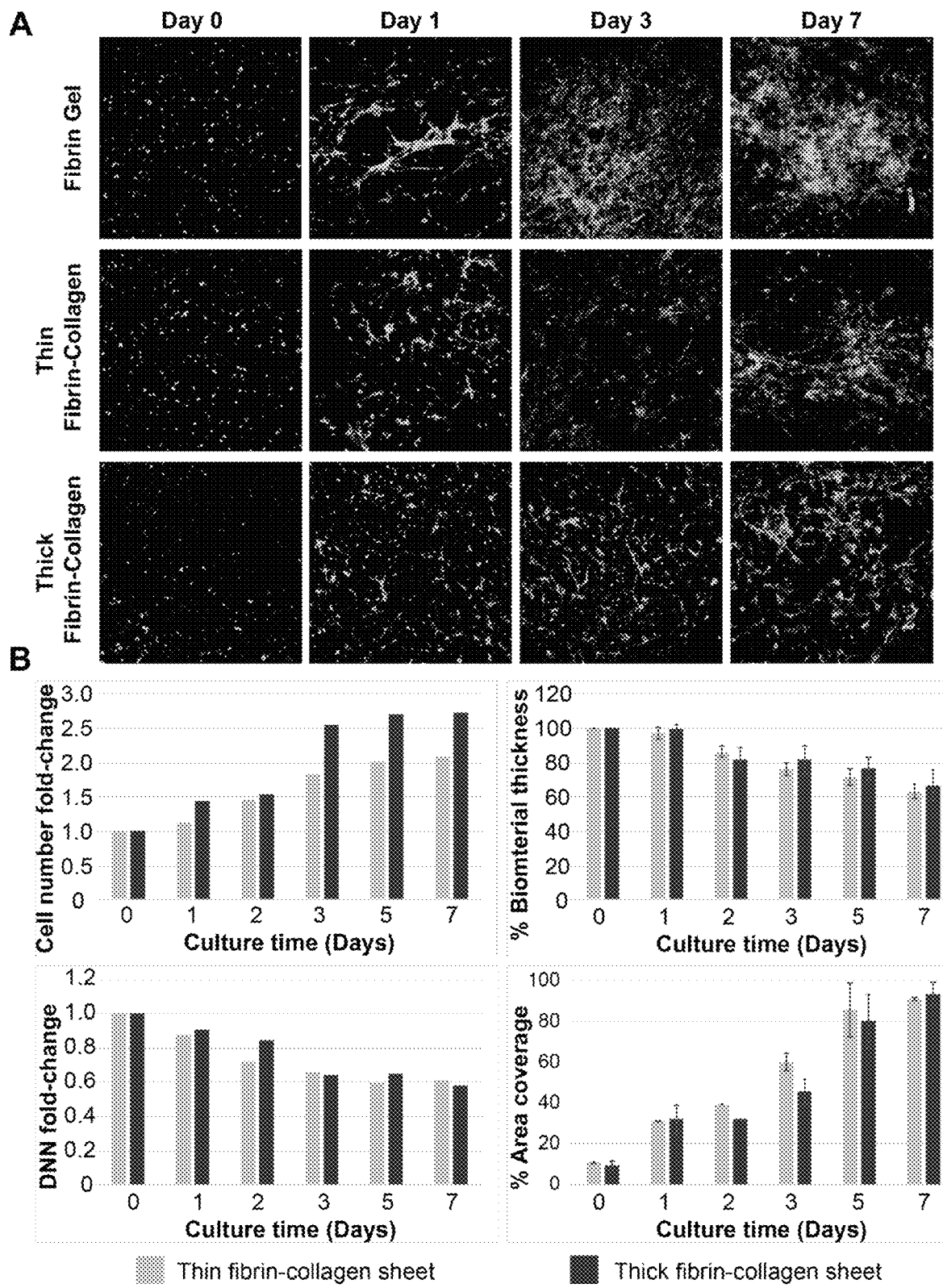
FIG. 19 is a micrograph image of human cells cultured in thermally gelled fibrin-collagen materials as enabled by the temperature control handheld bioprinter embodiment. Immunostaining of cells over one week of 3-D culture, and quantification of distance to nearest neighbor, cell number, area coverage, and material degradation are shown in a graph format.

Various embodiments and aspects of the disclosure will be described with reference to details discussed below. The following description and drawings are illustrative of the disclosure and are not to be construed as limiting the disclosure. The drawings are not necessarily to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

Parts List

The device will be described with respect to the FIGS. in which the reference numerals refer to the following parts.
02. Cell and biomaterial containing syringe 1
04. Crosslinker containing syringe 2
06. Microfluidic printhead
08. Roller
10. Stepper motor driving syringe 1
12. Syringe plunger 1
14. Syringe plunger 2
16. Stepper motor driving syringe 2
18. Scaffold coolant port
20. Stepper motor driving wheel
22. Handheld interface
24. Handheld coolant port 1
26. Handheld coolant port 2
28. Wheel frame
30. Button input
32. Bevel gear
34. Printhead interface
36. Printhead interface coolant port
38. Roller coupler
40. Rod frame
42. Stabilizer spring
44. Torsional spring
46. Spring coupler
48. Positional screw
50. Coolant tubing
52. Material tubing
54. Skin wound
56. Biomaterial sheet
58. Crosslinker sheet
60. Handheld interface printed control board
62. Coolant
64. Coolant hose
66. Gimbal
68. Syringe interface The handheld printer disclosed herein is comprised of four modules: the printhead system, the roller drive system, the syringe drive system, and the control system. Each will be described in detail herebelow.

Printhead System/Mechanism

The printhead system is comprised of two components: the printhead (06) ("microfluidic device/chip"), and the printhead interface (34) (which is shown as a metal bracket/holder in the FIGS.). The printhead is connected to the handheld printer through the printhead interface, and the printhead interface is attached to the handheld printer frame. In an embodiment, the printhead is connected to the printhead interface via physically clipping on by hand. Other embodiments to attach the printhead to the printhead interface may include adhesive, spring, or other mechanical latch systems, by hand or with additional tools.

The printhead interface is mechanically coupled to the frame of the handheld printer with n-degrees of rotational freedom and attached by hand. In the preferred embodiment, the printhead interface is a two-axis gimbal design (66) with two degrees of rotational freedom, in the X-Y and Z axis to guide the printhead as it translates over arbitrarily large and inclined skin wounds (54). By pressing the 2 DoF print-head against substrate, the torsional spring (44) attached to the spring coupler (46) absorbs the compression energy, the chip holder rotates upward around the shaft, and by releasing the pressure on the substrate, the torsion spring provides 3.4-newton*cm torque in average, gently force the chip holder rotates downward around the shaft to ensure a continuous contact with the deposition surface. This is defined as the first Degree-of-Freedom (the "1st DoF") of the print-head. It enables the printer to print over arbitrary curvatures that are parallel to the printing direction (the "x rotation axis"), without constantly adjusting operator's arm. The 1st DoF is capable of 80-degree rotational motion.

By rolling the printhead over curvatures that are lateral to the printing direction, the chip holder will freely adjust its angle about the metal pin, and compliant the lateral curvature. This is defined as the second Degree-of-Freedom (the "2nd DoF") of the print-head. The print-head is capable of 50-degree rotational motion. Other embodiments may include additional degrees of rotational freedom, and attachment to the frame either by hand or with additional tools.

The printhead interface also has a hollow internal structure, which allows fluid to flow through for temperature regulation. In the preferred embodiment, coolant (62) flows from the external chiller through a coolant hose (64) into the handheld bioprinter via the coolant port 1 (24) and coolant port 2 (26). The coolant then fills the internal structure of the handheld bioprinter and exits through the scaffold coolant port (18), past the coolant tubing (50), and enters the printhead interface through the printhead interface coolant port (36). through which reduces the temperature of the printhead to 4 degrees Celsius, enabling the deposition of temperature-sensitive collagen-I bioinks without premature gelation, only gelling after it exits the printhead and is in contact with the wound substrate which is 37 degrees Celsius. Human cells delivered via this temperature-controlled handheld bioprinter embodiment can be cultured in vitro in thermally-gelling fibrin-collagen 3D constructs and maintained for at least one week. Other embodiments may include flow of liquids for heating purposes, or other temperature regulating approaches that do not require an external chiller such as direct application of phase-change material packs.

The printhead is a nozzle which directs the flow of materials and/or crosslinker into the desired shape. In the preferred embodiment, the printhead is a 3D-printed resin microfluidic device with an internal branching structure which organizes the bioink and crosslinker that flow from the syringes through the material tubing (52) into biomaterial sheets/tissue precursor sheets (56) with patterns such as alternating stripes or multiple material composition layers after gelation with the co-delivered crosslinker sheet (58). The cellular component of the biomaterial sheet in an embodiment includes an optimized cell concentration of $1\times10^6$ cells/ml of 20 mg/ml fibrin and 1% hyaluronic acid biomaterial, determined from a cell concentration range of $5\times10^3$ to $5\times10^7$ cells/ml. Other embodiments may include delivery of therapeutics including vascular endothelial growth factor (VEGF), basic fibroblast growth factor (bFGF), epidermal growth factor (EGF), platelet-derived growth factor (PDGF), in addition to integrating optical fibers in the printhead interface for in-situ deposition of biopolymer solutions and bioinks with light induced gelation. For example, light from a light emitting diode (LED, emission wavelength either 365 nm or 470 nm) can be coupled into a fiberoptic cable bundle. The fibers can be linearly arranged via individual groves in a 3D printed region ("light cartridge"). The light cartridge can be attached above the printhead with the linear fiber array at its end arranged in parallel with the microchannel array at the exit of the microfluidic cartridge. The emitted light sheet illuminates the newly deposited bioink layer, inducing solidification of the bioink via photocrosslinking.

Roller Drive System

The roller drive system is comprised of two components: the roller (08) ("soft/silicone wheel"), and the roller interface ("roller coupler (38), rod frame (40), bevel gear (32), stabilizer spring (42), positional screw (48), and wheel frame (28)"). The roller is connected to the handheld printer through the roller coupler, and the roller coupler is attached to the handheld printer frame. In the preferred embodiment, the roller is connected to the roller coupler via physically sliding through a 316-stainless steel rod and securing the position with a 4-Newton stabilizer spring. The roller coupler is attached to the handheld printer frame through a rigid arm. Other embodiments to attach the roller to the roller coupler, and the roller coupler to the handheld printer frame, may include adhesive, spring, or other mechanical latch systems, by hand or with additional tools. The roller is an object which guides the handheld printer across the surface at a pre-determined speed via a stepper motor (20). In an embodiment, the roller is a soft silicone rubber wheel sized 36 mm in diameter, and 24 mm in width.

The wheel material is Smooth On Ecoflex shore OO-20, moulded from 3D printed Nylon 12 Shore OO-20, and is driven by a stepper motor. This wheel achieves a large contact area with the wound and thereby reduces the contact pressure during the deposition process. With the width of the wheel sized smaller than the microfluidic device exit, the printer capable of printing over large wound sites by applying multiple deposition paths side-by-side without running over previously deposited sheets. Other embodiments may include wheels of different material composition with various stiffness values linked to a range of contact pressures on the substrate, driven passively ("manually rotating") or actively ("motor driven").

Syringe Drive System

The syringe drive system is comprised of two components: the syringes, and the syringe interface (68) ("syringe scaffold"). The cell and biomaterial containing syringe (02) or the crosslinker containing syringe (04) is connected to the handheld printer through the syringe interface, and the syringe interface is attached to the handheld printer frame. In the preferred embodiment, the syringe is connected to the syringe interface via physically attaching through a physical slot and secured in position with a notch. The syringe interface is attached to the handheld printer frame through using screws. Other embodiments to attach the syringe to the syringe interface, and the syringe interface to the handheld printer frame, may include adhesive, spring, or other mechanical latch systems, by hand or with additional tools.

The syringe drive system pushes the plunger on the syringe at a preferred rate. In the preferred embodiment, a stepper motor (10) drives the cell and biomaterial containing syringe (02) by pushing on the syringe plunger (12). A second stepper motor (16) drives the crosslinker containing syringe (04) by pushing on a parallel syringe plunger (14). These stepper motors actively drive the individual plunger motion at different, controllable speeds. Other embodiments may include one or more stepper motor driven, pneumatic, hydraulic, or other methods of dispensing the fluid in the syringe at a predictable rate, in combination or in isolation.

Temperature control for the syringe consists of a lightweight jacket that conducts, and isolates heat away from the syringe. The system is intended for applications where materials in the syringe are sensitive to external temperature. The jacket temperature is controlled by a solid-state thermoelectric cooler, a coolant loop/water block, or phase-change materials. The temperature control jacket in is a thin metal frame that conforms to the surface of the syringe. It is either flexible and thin to allow for conformation or movement of the syringes or rigid and hollow. The primary mode of heat transfer, which allows for temperature control, is by conduction between a good thermal conductor (metal jacket) and the poor conducting surface of the syringe (plastic, glass, or related materials). The syringe is then cooled indirectly by the cooling of the jacket material.

The cooling of the jacket material is either performed by the thermoelectric effect (solid-state), convective heat transfer via a moving coolant like glycol or by the phase change of a refrigerant like propane or a by a polymeric phase change material. At the chiller, a fan guides air towards a heat sink. Warm exhaust air is isolated from main body by plastic forms and guided away from syringes. A cooled working fluid passes through a water block that is held to syringes. The coolant is held at desired temperature or below using a compressor loop and refrigerant or by a thermoelectrically driven chiller. The coolant loop allows for a smaller package by removing the cooling components from the handheld device. It also allows for direct device cooling via convection by the working fluid. Removing the cooling from the body of the handheld printer allow for a more powerful cooling loop to be fitted and remove mechanical components to a location away from the patient or surgeon. The water block is printed via DMLS or a similar metal additive manufacturing process or made from two machined pieces of metal with a gasket. Single-Part additively manufactured stainless steel part improves autoclavability of system.

Control System

The control system is comprised of a controller system where operating conditions of the roller drive system and syringe drive system can be changed, and a power supply. In an embodiment, there is an external control unit where the operator can control operating conditions of the roller drive system and the syringe drive system, in addition to a printed control board situated within the handle of the handheld printer (60). The external controller ("computer") is connected via mains electrical supply. Other embodiments may include on-board controllers only (with no external controller), with battery supply.

Handheld Switch

This is the switch ("button input") (30) which resides in the handheld interface ("handle") (22) of the printer. When triggered, given that none of the limit switches are tripped, the motor will start to turn and drive the printing operation.

ps Biomaterial Syringe Limit Switch

This is the limit switch that is installed at the end of travel of the bio-material syringe. The purpose of the limit switch is to detect the depletion of material and stop the motor before damage happens.

Crosslinker Syringe Limit Switch

This switch is similar to biomaterial syringe limit switch but for crosslinker syringe.

User Interface (UI) Button Array

To allow user to change settings on the fly, there are a set of tactile buttons connected to microcontroller through I2C bus. The up and down buttons are for adjusting value higher or lower by fix increment or decrement. The left and right buttons are for selecting which settings to adjust. The select button brings the user to the page of the selected setting and enable the up and down buttons for value adjustment. Once change is done, press the select button again will register the change and back to main page on LCD display. The reset button is for resetting everything back to default. It will cause the printer controller (microcontroller) to reboot.

MCU

This is the microcontroller unit which manages all of the logic of operation. The control logic was implemented as state machine. Different state of the input signals (listed above) will trigger the microcontroller to switch to different state of operation.

Motor Controller

Motor controller is the unit that converts the direction and PWM (pulse width modulation) signal generated by the microcontroller to motor rotation direction and speed. It also has built-in thermal protection and voltage protection features. There is a motor controller for each motor.

LCD Display

The liquid crystal display (LCD) is used to display settings to user for reference during operation. It is also used to guide the user through the process of updating change using the buttons.

Motor

The motor is the unit that converts electrical power into mechanical motion according to the microcontroller instruction. There are three motors in the printer design. Two of them are for driving two different syringes to deliver printing materials. The other is for driving the roller to guide operator to print at a constant speed across patient's skin surface.

In summary, the present disclosure provides a printing device for dispensing materials used for healing injuries to skin, such as burns and the like. The device disclosed herein is designed to be handheld but it will be understood that it could be designed to be held, manipulated and used by a robotic arm or any other type of positioning device.

The handheld embodiment of the printing device is comprised of a handheld interface, a syringe drive system mounted on a rail structure mechanism on the handheld interface. The device includes a syringe interface which can be designed for one or more syringes. The number of syringes used will depend on the type of skin injuries anticipated to be treated by the printer. The device includes a printhead interface mounted to the handheld mounted on a gimbal mechanism which is configured to provide one (1), two (2) or three (3) degrees of freedom of a printhead which is mounted to the printhead interface. The printhead is designed with a plurality of exits along its length. The length of the printhead can very from narrow (millimeters to a centimeter) for treating small or very local skin injures, or greater than a centimeter for treating larger area skin injuries. The printer includes a deformable axle mounted wheel made of a polymer material such as silicone rubber. The deformable wheel may be ridged, or have any other type of surface texturing.

The deformable axle mounted roller is mounted or placed behind the printhead, and its width may be equal, or narrower to the strip of deposited materials in order to reduce the contact pressure and increases the traction to the substrate. The wheel is mechanically coupled to a rigidly fixed motor mounted on the handheld device. When the wheel is in contact with the surface and the operator is holding the handheld printer and the motor is switched on, the wheel pushes the handheld printer towards the operator along the substrate surface. The wheel can be mechanically coupled and decoupled without obstruction via quick connect couplings, thus allowing addition or removal without tools by the operator. The wheel in contact with the wound is preferably disposable, sterilizable, and biocompatible. The wheel drive system is preferably sterilizable, disposable, and biocompatible.

The printhead (microfluidic chip) that may or may not be disposable is attached via a quick connect mechanism to the printhead interface such as a holder plate where it is rigidly mated in place and does not move relative to the holder. A bevel gear motion transmission as a drive mechanism on the printhead to laterally translate the handheld bioprinter on soft or stiff substrates. The printhead may be a two or more component printhead for mixing, dispensing multiple liquids and reagents including cells, proteins, and other inorganic or organic materials In an embodiment the printhead can be attached or detached by hand without tools and being made of a rigid polymer material can have a V-groove to slightly deform when mated to the edge of the holder plate it snaps into place and held there by a friction fit. The holder plate is mounted to the gimbal mechanism which is mechanically coupled to the handheld portion and the gimbal mechanism provides with orientational and positional freedom of motion. This advantageously holds the elongate exit edge of the printhead against the injured tissue as the mixture of therapeutic agents and being dispensed to the injury from digging into, or putting undue pressure on the injured area of the patient. Put another way, when the deformable wheel is in contact with the injured surface, the gimbal device is configured to resist lifting of the printhead off the surface as well as preventing it from applying excessive pressure to the injured site.

The gimbal assembly/mechanism is configured so that when the wheel is travelling along the surface, the gimbal also resists changes about the axis of travel and maintains contact across the width of the device through its gimble mechanism. The device facilitates maintaining an angle/orientation independent of the angle/orientation of the handheld printer. Since the printhead is on a separate axis from the roller, the weight of the printer and/or any additional operator-induced downwards force does not impact the positioning of the printhead. In other words, the printhead is not rigidly connected to the wheel component, such that downwards force is distributed by both components and where the printhead would "dig" into the wound. In this embodiment, the printhead supplies a constant force enough to only slightly deform the substrate to maintain contact across the width of the printhead, independent of the applied force on the roller to maintain traction with the substrate.

The printer is configured to control the temperature of the printer and its contents, for example the holder is preferably a hollow metal plate having an entrance and exit for cooling or heating fluid to pass through the holder for cooling or heating the printhead, with the action of heating or cooling being dependent on the liquid cell mixture being dispensed.

The printer is configured to integrate and include an optical interface for illumination of the printed material in applications where for example light-induced gelation at the printhead exit is needed. For example, optical fibers coupled to a light source may be mounted on the printhead itself focused to the printed material. An array of fibers mounted side by side along the length of the printhead or holder to illuminate the dispensed material.

As noted above, there may be one or more syringes depending on the nature of the injury being treated. The printer device is configured such that the syringes are temperature controlled. A temperature control unit on the handheld device surrounds the syringe jacket. In one embodiment they may all be controlled by one temperature control loop when the liquids are being dispensed at the same temperature. Alternatively, they may each be controlled separately in the event the liquids/mixtures are to be dispensed at different temperatures. The syringe jacket is self-contained, packaged, and sterilizable separately and mounted to the handheld device such that it can be detached by hand.

The printer device is configured so that the plunger of each syringe can be driven or activated by an electric motor and where multiple syringes are used multiple motors are mounted to the housing portion. The syringe(s) are separate and distinct from rest of the printer assembly and can be detached by hand.

The handheld interface contains a manual touch interface (button or passive touch). The handheld interface is designed and configured to interface electronically with both the wheel drive system and the syringe drive system and/or the computer control system. The control system is programmed with software instructions to correlate the speed of the roller with the amount of material being printed and a user interface allows a user to select all parameters such as speed, dispensing rate, temperature of the printhead and the liquids being dispensed.

The computer control system may be configured to be on-board the handheld system by for example microprocessors contained within the handle of the device or it may be a stand-alone unit external to the device which is electronically interfaced with the individual components off-board.

The handheld print device may be configured to be powered externally by standard electrical connections to the power mains or internally by battery contained within the handle portion of the device.

Therefore what is claimed is:

1. A bioprinter for controlled in-situ formation and deposition of any one or combination of biopolymeric sheets, therapeutic agents and planar tissues on surfaces on surfaces, comprising:
   a) support frame and a gimbal attached to said support frame and a printhead attached to said gimbal, said printhead including a first array of extrusion channels and a gelation means located with respect to said first array such that in operation said gimbal positions said printhead such that said first array is in physical contact with said surface regardless of the contour of said surface, an end section of said printhead having a width W such that said first and second arrays span said width W;
   b) a first reservoir containing a biopolymer, said first reservoir being operably attached to said frame, said first array of extrusion channels being in flow communication with said first reservoir such that said biopolymer is configured to be extruded onto the surface, a first dispensing mechanism associated with said first reservoir being configured to dispense biopolymer at a flow rate of QM;
   c) a drive mechanism attached to said frame including a soft roller, said drive mechanism such that when activated by the operator, said printhead is driven along the surface at a preselected velocity V by said soft roller;
   d) a controller connected to said drive mechanism and said first dispensing mechanism and said gelation means and programmed such upon activating said drive mechanism, and when said first dispenser includes biopolymer, said dispensing mechanism dispenses biopolymer at the flow rate QM a layer of thickness t and said gelation means gelates said biopolymer on said surface.

2. The bioprinter according to claim 1, wherein said drive mechanism is configured to provide variable velocities V, and wherein said controller is programmed with instructions to control said first dispensing mechanism to responsively adjust said flow rate QM such that for a given velocity V said flow rate conditions are maintained.

3. The bioprinter according to any claim 1, wherein said exit section of said printhead including an overhanging section extending outwardly from a top surface of said second array, said overhanging protruding section extending outwardly from said exit section by a length L.

4. The bioprinter according to claim 1, wherein said first array of extrusion channels are in flow communication with said first reservoir via a bifurcating channel network comprised of a first channel connected to said first reservoir which bifurcates into two channels which further bifurcates until a final number of channels equals a number of extrusion channels in said first array, and an end of each channel is adjacent an end of a corresponding extrusion channel in said first array.

5. The bioprinter according to claim 4 wherein hydraulic diameters of the channels in the bifurcating channel networks decrease from each inlet to each exit going from said reservoir to said printer head in accordance with Murray's law.

6. The bioprinter according to claim 1, further comprising a handle for allowing a user to grasp and use the bioprinter during dispensing operations so that the bioprinter is a handheld bioprinter.

7. The bioprinter according to claim 1, wherein a printhead interface is attached to said gimbal and said printhead is removably attachable to said printhead interface.

8. The bioprinter according to claim 7, wherein said printhead is secured to said printhead interface by a printhead quick release mechanism.

9. The bioprinter according claim 1, wherein said soft roller is removably attachable to said drive mechanism.

10. The bioprinter according to claim 9, wherein said soft roller is secured to said drive mechanism by a roller quick release mechanism.

11. The bioprinter according to claim 1, wherein said first reservoir is removably attachable to said frame.

12. The bioprinter according to claim 1, wherein when in operation said gimbal is configured such that said printhead exerts a force on said surface that is independent of the force that said soft roller exerts on said surface.

13. The bioprinter according to claim 1, wherein said gimbal is a two-axis gimbal.

14. The bioprinter according to claim 1, wherein said gelation means is a liquid gelation means including a second reservoir containing a gelation liquid, said second reservoir being attached to said frame, said printhead having a second array of extrusion channels being in flow communication with said second reservoir such that said gelation liquid is configured to be extruded along with said extruded biopolymer, and a second dispensing mechanism associated with said second reservoir being configured to dispense the liquid at a flow rate of QC, wherein said controller is connected to said second dispensing mechanism and programmed such upon activating said drive mechanism, said second dispensing mechanism dispenses biopolymer at the flow rate QM.

15. The bioprinter according to claim 14, wherein said second array of extrusion channels are in flow communication with said second reservoir via a bifurcating channel network comprised of a first channel connected to said second reservoir which bifurcates into two channels which further bifurcates until a final number of channels equals a number of extrusion channels in said second array, and an end of each channel is adjacent an end of a corresponding extrusion channel in said second array.

16. The bioprinter according to claim 14, wherein said second reservoir is removably attachable to said frame.

17. The bioprinter according to claim 1, wherein said gelation means is a light induced gelation means including a light source configured to emit light and a light emitter in optical communication with said light source, wherein said biopolymer is photopolymerizable, and wherein said controller is connected to said light source and programed such upon activating said drive mechanism, said light source emits light and said light emitter directs said light onto said surface such that said biopolymer gelates via photo cross-linking.

18. The bioprinter according to claim 17, wherein said light source is a plurality of light sources and said light emitter is a plurality of light emitters.

19. The bioprinter according to claim 17, wherein said light source is a remote light source attached to said frame and said light gelation means further includes a light transmission means configured to transmit light from said light source to said light emitter.

20. The bioprinter according to claim 19, wherein said light transmission means comprises at least one optical fiber.

21. The bioprinter according to claim 17, wherein said light source and said light emitter are a combined light source and emitter operably attached to said printhead.

22. The bioprinter according to claim 1, wherein said bioprinter further includes a temperature control system configured to control the temperature of said biopolymer.

23. The bioprinter according to claim 22, wherein said temperature control system includes a printhead temperature control means is operably attached to said printhead, and said printhead temperature control means connected to said controller and programed such that the user can control the temperature of said biopolymer in said printhead.

24. The bioprinter according to claim 22, wherein said temperature control system includes a first temperature control jacket is operably attached to said frame, said first temperature control jacket is connected to said controller and programed to adjust the temperature of said first temperature control jacket such that the user can control the temperature of said biopolymer in said first reservoir.

25. The bioprinter according to claim 22, wherein said temperature control system one of a solid-state thermoelectric device, a temperature regulation loop containing a working heat exchange fluid, or phase-change materials.

26. The bioprinter according to claim 23, wherein said gelation means is a temperature induced gelation means, and wherein said biopolymer is cooled in said printhead such that said biopolymer gelates upon being dispensed onto said surface.

27. The bioprinter according to claim 1, wherein upon activating said drive mechanism, said soft roller has a contact patch with said surface having a width WR, wherein said printhead width W is greater than said contact patch width WR.

28. The bioprinter according to claim 1, wherein said controller has an interface to control at least one of said operation parameters.

29. The bioprinter according to claim 1, wherein said gimbal is a three-axis gimbal to provide three (3) degrees of freedom motion.

30. The bioprinter according to claim 1, further comprising a preselected additional number of reservoirs, each reservoir having a dispensing mechanism associated therewith.

31. The bioprinter according to claim 1, wherein each reservoir is heated or cooled by a single heating or cooling source.

32. The bioprinter according to claim 1, wherein each reservoir is heated or cooled independently of the other reservoirs by separate heaters or coolers.

33. The bioprinter according to claim 1, wherein said therapeutic agents are precursors of biopolymeric sheets and planar tissues.

34. The bioprinter according to claim 1, wherein said at least a first reservoir is a syringe.

35. The bioprinter according to claim 1, wherein said bioprinter is configured, shaped and sized to be held by a human hand, or it may be configured, shaped and sized to be held by a robotic hand or end effector.

36. A method of applying therapeutic agents to injured skin using the device according to claim 1, comprising:
   selecting a liquid mixture having a therapeutic agent mixed therein and filing said at least first reservoir;
   programming the controller to provide a preselected flow rate of the therapeutic agent being dispensed from the reservoir and a preselected velocity of the drive mechanism of the soft roller; and
   activating both said first dispensing mechanism to dispense the therapeutic agent and said drive mechanism to rotate said soft roller causing said bioprinter to dispense said therapeutic agent.

* * * * *